US00PP18960P2

(12) United States Plant Patent
Sheehan

(10) Patent No.: US PP18,960 P2
(45) Date of Patent: Jun. 17, 2008

(54) GRAPEVINE ('SHEEGENE-5')

(50) Latin Name: *Vitis vinifera*
Varietal Denomination: Sheegene-5

(76) Inventor: Timothy P. Sheehan, 120 Olivewood Ct., Porterville, CA (US) 93257

( * ) Notice: Subject to any disclaimer, the term of this patent is extended or adjusted under 35 U.S.C. 154(b) by 0 days.

(21) Appl. No.: 11/708,799

(22) Filed: Feb. 20, 2007

(51) Int. Cl.
*A01H 5/00* (2006.01)

(52) U.S. Cl. ..... Plt./205
(58) Field of Classification Search ..... Plt./205
See application file for complete search history.

*Primary Examiner*—Annette H Para
(74) *Attorney, Agent, or Firm*—Baker Manock & Jensen, PC; Eric C. Cole

(57) ABSTRACT

A new and distinct variety characterized by large, red-colored seeded grapes that ripen in late July, approximately six weeks earlier than Red Globe (U.S. Plant Pat. No. 4,787), when grown in the San Joaquin Valley of Central California. The grapes of this new variety are produced on strong stems and branches and are well adapted to commercial handling.

1 Drawing Sheet

Latin name of the genus and species of the plant claimed: The claimed plant relates to a new and distinct variety of *Vitis vinifera* to be known as 'Sheegene-5'.

Variety denomination:

The new variety of *Vitis vinifera* is the result of hybridization of 'Princess' (unpatented), the pollen parent, and 'Red Globe' (U.S. Plant Pat. No. 4,787), the seed parent. The new variety was first hybridized by Timothy P. Sheehan of Porterville, Calif. in the Spring of 2000. The new variety was asexually propagated in the dormant season of 2003, bud grafted on 'Harmony', virus-free rootstock near Fowler, Calif. Four vines were planted in a *Vitis vinifera* variety block located near Fowler, Calif. on the west side of Thompson Road, north of Adams Road. The red-colored seeded grapes produced by the new variety are large in size, with good to excellent flavor. The new variety has been shown to maintain its distinguishing characteristics through asexual propagation.

BACKGROUND OF THE INVENTION

The present invention relates to a new and distinct variety of grape which will hereinafter be denominated as 'Sheegene-5' and more particularly as a grapevine which produces a large, red-colored seeded grape that matures during late July in the San Joaquin Valley of Central California. The new invention resembles 'Red Globe' (U.S. Plant Pat. No. 4,787).

SUMMARY OF THE INVENTION

The 'Sheegene-5' grapevine is characterized by producing a large, red-colored seeded grape which has very good flavor, and it is highly productive and mature for harvesting and shipment during late July in the San Joaquin Valley of Central California. The new variety of table grape can be compared to 'Red Globe' (U.S. Plant Pat. No. 4,787) but the grapes mature approximately six weeks earlier and are large in size, among other distinguishing characteristics.

BRIEF DESCRIPTION OF THE DRAWING

The accompanying drawing is a color photograph that displays mature leaves both at the top and bottom of the right side, small leaves with tendrils at the top on the left, a cluster of the mature grapes on the left in the center, two immature small clusters below on the left, in the center four grapes cut in half displaying the color of the flesh and the shape of the berries, in addition to a short mature branch displaying its color in the center on the right side.

DETAILED BOTANICAL DESCRIPTION

Referring more to the horticultural description of the new and distinct variety of grapevine, the following description has been observed under the ecological conditions prevailing at the origin vineyard which is located near Fowler, Calif. in the San Joaquin Valley of Central California.

All major color designations are by reference to the Dictionary of Color by Maerz and Paul, First Edition, published in 1930. Common color names are also used in several instances.

Vine:

*Size.*—Large for four year old vine.
*Vigor.*—Very good.
*Chilling requirements.*—Normal for grapevines in the San Joaquin Valley of Central California.
*Figure.*—With wide cordons forming a T-shape figure.
*Production capacity.*—Very good.
*Regularity of bearing.*—Regular.

Trunk:

*Size.*—10 inches (25.4 cm) in circumference, 20 inches above graft.
*Surface texture.*—Rough, shaggy.
*Color of bark.*—Pl.7 H9 Liver Brown and Autumn Oak.
*Mature canes.*—Color: Pl.14 L12 Sudan Br.
*Nodes.*—Four to five nodes on cane.
*Length between nodes.*—4 to 6 inches (10.16 to 15.24 cm).
*Lenticels.*—Number: 0.
*Lenticels.*—Size: 0.
*Shoot length.*—3¼ inches (8.89 cm).
*Shoot shape.*—Drooping.
*Tendrils.*—Number: 3 to 5.
*Tendril.*—Size: 2 to 4 inches (5.05 to 10.16 cm).

*Tendrils.*—Location: At nodes.
*Tendrils.*—Form: Bifurcate.
*Tendrils.*—Texture: Firm.
*Bud shape.*—Convex.
*Bud size.*—Small, 3/16 inches (4.71 mm) in length, 4/16 inches (6.35 mm) in width.
*Bud fruitfulness.*—Very good.

Branches:
*Size.*—3 inches (7.62 cm) in circumference.
*Cordons.*—33 to 48 inches (96.5 to 121.92 cm) from trunk.
*Color.*—One year or older wood: Pl.7 El1 Trotteurtan, Malabar Mummy Br.+Bay.
*Color.*—Immature Branches: Pl.20 C9 Piquant gr.

Leaves:
*Size.*—Generally large.
*Density.*—Dense.
*Average length.*—7¾ inches (19.69 cm).
*Average width.*—8¼ inch (20.96 cm).
*Form.*—Pentagonal.
*Texture.*—Upper Surface: Smooth.
*Color.*—Upward Disposed Surface: Pl.23 J9 Polo green.
*Color.*—Lower Disposed Surface: Pl.20 K7 Near Piquant green.
*Leaf vein.*—Color: Pl.20 K6 Piquant green.
*Marginal form.*—Generally slightly undulated.
*Leaf vein.*—Thickness: 2 mm (0.079 inches).
*Glandular characteristics.*—None.
*Petiole size.*—Large.
*Petiole length.*—14 cm (5.25 inches).
*Petiole thickness.*—5 mm (0.197 inches).
*Petiole color.*—Pl.20 K6 Piquant green on part of petioles with Pl.5 I9 Bois de Rose on part of circumference of the petiole.
*Petiole sinus form.*—Upside down U-shape.
*Lobe* (*average*).—Four.
*Tooth size.*—10 to 20 mm (0.39 to 0.79 inch) in length; 15 to 20 mm (0.39–0.79 inch) width.
*Tooth number.*—Four between lobes.
*Teeth shape.*—Convex.

Inflorescence:
*Size.*—135 to 170 mm (5.32 to 6.69 inches).
*Number born.*—Per Spur: 2 to 3.
*Number born.*—Per Vine: Many.

Flowers:
*Flower buds.*—Small.
*Flower buds.*—Surface: Glabrous.
*Flowers.*—Generally: Heavy.
*Date of bloom.*—May 13, 2006.
*Date of full bloom.*—May 17, 2006.
*Size.*—5 to 6 mm (0.20 to 0.24 inches).
*Petals color.*—Pl.7 C8 Mauve Taupe Copra.
*Petals size.*—Small; 3 mm (0.12 inches).
*Pistil color:*Pl.17 L7 Viridine Y.
*Date visible borne berry set.*—May 18, 2006.
*Size.*—3 mm (0.12 inches).

Fruit:
*Solids.*—18.6° Brix.
*Acids.*—0.52.
*Sugar/acid ratio.*—35.7.
*Juice pH.*—3.74.
*Seeds.*—Yes.
*Seed number.*—2 to 3.
*Capstem pedicel.*—10 to 12 mm (0.39 to 0.47 inches).
*Berry weight.*—8.52 grams.
*Juice color.*—Pl.D7 Rose Breath.
*Cluster size.*—Small to medium.
*Cluster average length.*—12.07 to 19.69 cm (4¾ to 7¾ inches), not including main stem of cluster.
*Cluster average diameter.*—12.7 cm (5 inches) at greatest width.
*Cluster weight.*—482.8 grams (17 oz.).
*Compactness.*—Compact.
*Cluster form.*—Conical.
*Stem.*—Generally: 8.5 cm (3.35 inches) in length.
*Stem.*—Calpher: 4.5 mm (0.177 inches).
*Berry.*—Size: Medium to large.
*Berry.*—Form: Ovate.
*Berry numbers.*—55 to 60.
*Berry size.*—Average: 26 mm (1.02 inches), as measured along the longitudinal axis; 25 mm (0.98 inches), as measured along the transverse axis.

Skin:
*Thickness.*—Thin.
*Texture.*—Tough.
*Tendency to crack.*—None known.
*Blush color.*—Pl.55 L8 Rubient.
*Ground color.*—Pl.55 H4 Wineberry.
*Pulp.*—Clear to PL.7 E9 Kaffa Hampstead Brown.
*Lenticels.*—None.

Flesh:
*Color.*—Pl.6 I8 Slate V.
*Juice production.*—Very good.
*Flavor.*—Very good.
*Aroma.*—Very mild.
*Texture.*—Firm.
*Ripening.*—Even.
*Eating quality.*—Very good.
*Use.*—Fresh Market.
*Keeping quality.*—Good.
*Resistance to disease.*—Unknown.
*Harvesting.*—Late July.
*Shipping and handling qualities.*—Very good.

Having thus described and illustrated our new variety of grapevine, we claim:

1. A new variety of grapevine to be known as Sheegene-5 and parts thereof, substantially as illustrated and described, characterized principally by its production of large, red-colored seeded grapes, that mature approximately six weeks earlier than does Red Globe (U.S. Plant Pat. No. 4,787) which it resembles.

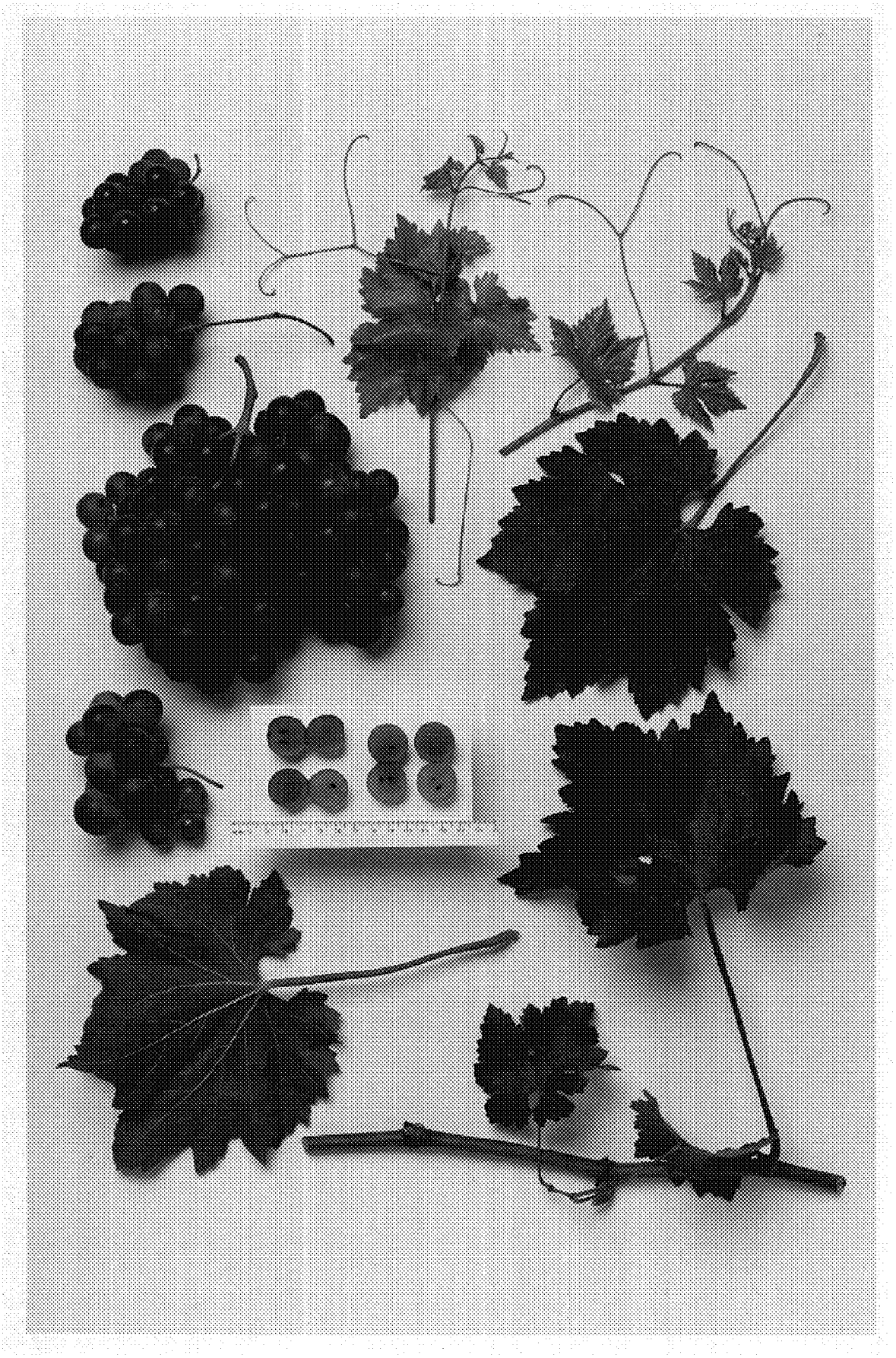

* * * * *